United States Patent [19]

Chu

[11] Patent Number: 5,885,526
[45] Date of Patent: Mar. 23, 1999

[54] ANALYTICAL DEVICE FOR MEMBRANE-BASED ASSAYS

[76] Inventor: Albert E. Chu, 140 Roblar Ave., Hillsborough, Calif. 94010

[21] Appl. No.: 823,936

[22] Filed: Mar. 25, 1997

[51] Int. Cl.[6] .................................................. G01N 33/543
[52] U.S. Cl. ............................... 422/56; 422/57; 422/58; 422/59; 422/60; 436/518
[58] Field of Search .................................. 422/56, 57, 58, 422/59, 60; 436/518

[56] References Cited

U.S. PATENT DOCUMENTS

| | | | |
|---|---|---|---|
| 4,632,901 | 12/1986 | Valkirs et al. | 435/5 |
| 4,818,677 | 4/1989 | Hay-Kaufman et al. | 435/4 |
| 4,965,187 | 10/1990 | Tonelli | 435/5 |
| 5,169,789 | 12/1992 | Bernstein | 436/501 |
| 5,185,127 | 2/1993 | Vonk | 422/56 |
| 5,296,192 | 3/1994 | Carroll et al. | 422/56 |
| 5,354,692 | 10/1994 | Yang et al. | 436/514 |
| 5,500,375 | 3/1996 | Lee-Own et al. | 436/514 |

*Primary Examiner*—Toni R. Scheiner
*Attorney, Agent, or Firm*—Flehr Hohbach Test Albritton & Herbert LLP

[57] ABSTRACT

An analytical device is provided. The device comprises a liquid-impervious top support layer that defines a rim around an open port. A porous reaction membrane having an upper surface and a lower surface is proximal to the top support layer, such that a portion of the reaction membrane upper surface and rim define a sample receiving well. The reaction membrane upper surface is sealed to the lower surface of the top support layer by water-insoluble adhesive so as to form a liquid-impervious seal therebetween. An absorbent body is proximal to and in liquid communication with the lower surface of the reaction membrane. The analytical device may further comprise a liquid-impervious bottom support layer which is attached to the lower surface of the absorbent body. The device can be used in immunoassays for the detection of a bindable substance in a liquid sample containing the target substance.

15 Claims, 5 Drawing Sheets

ANALYTICAL DEVICE FOR MEMBRANE-BASED ASSAYS

BACKGROUND OF THE INVENTION

The technical field of this invention concerns analytical devices for use in determining the presence of a bindable target substance (i.e. analyte) in a liquid sample suspected of containing such substance. Numerous analytical devices, in various configurations, have been used for this purpose. Many of these devices employ reaction membranes onto which a receptor capable of specifically binding to the target substance, is immobilized. In the assay that employs these types of devices, typically the sample to be tested is applied to the reaction membrane. If the target substance is present in the sample, it will bind to the immobilized receptor. Various methods are used to determine whether the target substance has bound to the receptor, thus indicating its presence in the sample. In one commonly used method, an antibody that is capable of specifically binding to the target substance and that is attached to a detectable label is applied to the membrane.

Membrane-based immunoassays and devices have greatly simplified medical diagnostics. In the past, enzyme-linked immunosorbent assays (ELISA) were the most common type of diagnostic assay. These assays were usually performed by skilled technicians in a clinical laboratory. With a typical ELISA, relatively long incubation times are required. Therefore, the assay usually takes over an hour to perform. Additionally, ELISAs are designed for testing samples in batches. Therefore, a sample is generally not tested until a sufficient number of samples have been obtained for testing. As a result, a patient may not receive test results until days after providing a sample. Membrane-based immunoassays have the advantage that they can be performed individually or in batch. Thus, a membrane-based immunoassays can be performed in a doctor's office rather than in a clinical laboratory. Individual tests can be performed, and results obtained, usually under 10 minutes. Quantitative results can also be provided by special instruments designed to read the test results.

The sensitivity of reaction-membrane type immunoassays (i.e. the ability to detect very low levels of target substance) can be increased if the sample is concentrated through the reaction membrane. With some devices, concentration of the sample through the reaction membrane is achieved by having an absorbent material beneath the reaction membrane that draws the sample, which is added to the top of the membrane, through the membrane and into the absorbent material below. Membrane-based immunoassays that utilize absorbent materials to concentrate sample are exemplified in U.S. Pat. No. 5,006,464 to Chu et al., U.S. Pat. No. 4,818,677 to Hay-Kaufman et al., and U.S. Pat. No. 4,632,901 to Valkirs et al., and U.S. Pat. No. 5,185,127 to Vonk et al.

The membrane and absorbent material of the analytical devices described in each of the patents referenced above are contained in a plastic housing having a top member and a bottom member which are joined together under compression to hold the membrane and absorbent material in place and in contact with each other. The use of sufficient compression facilitates the downward flow of the sample through the membrane. If there is insufficient compression, sample would tend to flow laterally across the membrane, thus reducing the amount of sample that flows through the center of the reaction membrane where the receptor is usually located. These types of analytical devices are typically assembled individually which can make the manufacturing process complicated and costly.

There is a continued need to further simplify membrane-based immunoassays and analytical devices therefor, as well as the analytical device manufacturing process to make them easier to use and more affordable. This is particularly true in developing countries, where a simple, rapid, sensitive, specific, storage-stable and economical diagnostic assay and analytical device would be ideal.

SUMMARY OF THE INVENTION

The present invention provides an analytical device that can be used in analytical assays, such as an immunoassay, for the detection of a bindable target substance in a liquid sample potentially containing the target substance. In its simplest embodiment, the analytical device comprises a liquid-impervious top support layer that defines a rim around an open port. A porous reaction membrane having an upper surface and a lower surface is proximal to the top support layer, such that a portion of the reaction membrane upper surface and rim define a sample receiving well. The reaction membrane upper surface is sealed to the lower surface of the top support layer by water-insoluble adhesive so as to form a liquid-impervious seal therebetween. An absorbent body is proximal to and in liquid communication with the lower surface of the reaction membrane.

The analytical device of the present invention may further comprise a liquid-impervious bottom support layer which is attached to the lower surface of the absorbent body.

DETAIL DESCRIPTION OF THE INVENTION

The present invention provides a simple, easy to manufacture analytical device for use in sensitive analytical assays for the detection of a bindable target substance in a liquid sample possibly containing the target substance. A water-insoluble adhesive is used to adhere a reaction membrane having a receptor bound thereon capable of binding to the target substance, and an absorbent body, to a liquid-impervious top support layer. The use of a water-insoluble adhesive not only serves the purpose of holding the device together structurally, but also forms a liquid-impervious seal which prevents lateral flow of liquid sample across the membrane surface to the extent that it forces the downward flow of the sample through the membrane and into the absorbent material. This type of sealing between the membrane and the liquid-impervious top support layer may also slow down the flow rate of the sample flowing laterally through the membrane thereby increasing the reaction time between the target substance and receptor, resulting in increased sensitivity.

Prior art analytical devices are often comprised of fitted upper and lower housing members which join together under compression, thereby holding the membrane in place between the open port and absorbent material. Examples of this type of analytical device are provided in U.S. Pat. No. 4,632,901, and U.S. Pat. No. 5,185,127. While such fitted housing members can be used in the practice of the present invention, the use of a water-insoluble adhesive to form a liquid-impervious shield makes the use of fitted housing members unnecessary. In another type of analytical device which, although does not use fitted housing members, the top and bottom support layers are heat-sealed together causing sufficient compression to hold the reaction membrane in place between the open port and absorbent material. An example of this type of device is shown in U.S. Pat. No. 4,818,677. Again, while this type of device can be used to practice the present invention, the use of a water-insoluble adhesive makes this unnecessary.

One advantage of not using compression to hold the reaction membrane in place between the open port and the absorbent material is that the upper surface of the reaction membrane remains relatively flat after the analytical device is assembled. Therefore, upon use, when the sample is added to the reaction membrane, the sample is more likely to evenly cover the entire exposed surface of the reaction membrane. Thus, if there are two or more regions of immobilized receptor on the membrane, approximately the same volume of sample will pass through each receptor area. In contrast, the use of compression to form a liquid impervious seal between the rim of the open port and the reaction membrane, can cause the upper surface of the reaction membrane to become slightly concave, or dome-shaped. Thus, when sample is added to the reaction membrane, it may not evenly cover the entire surface of the reaction membrane. This may make the device less suitable for some immunoassays where quantitative results are needed.

Figure 1:
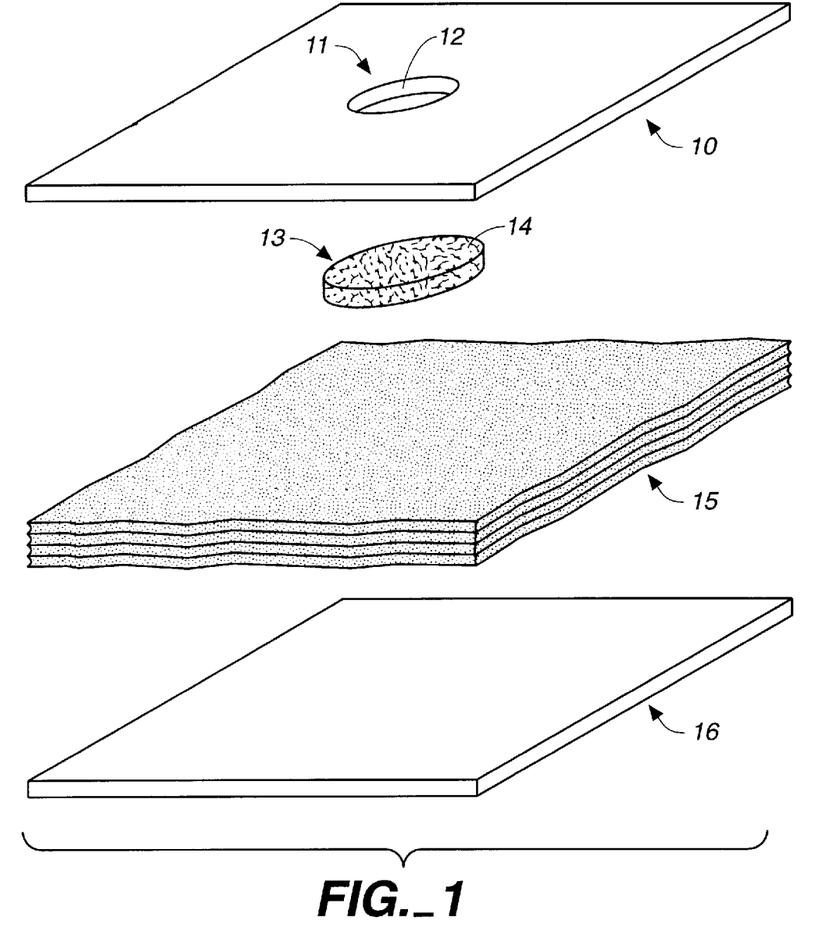
FIG. 1 is an exploded perspective view of an analytical device in accordance with the present invention showing the arrangement of the components of the device.

The analytical device is simple in construction, and can be made using readily available materials. Referring to FIG. 1, the analytical device comprises a liquid-impervious top support layer (10) that defines a rim (12) around an open port (11). A porous reaction membrane (13) is located beneath the top support layer such that, after the device is assembled, a sample receiving well is defined by the exposed upper surface (14) of the reaction membrane and the rim (12) around the open port (11). An absorbent body (15) is located beneath the reaction membrane. The device may further comprise a liquid-impervious bottom support layer (16) having an upper surface in contact with the lower surface of the absorbent body.

The top support layer can be formed from any water-impervious material such as metal, plastic or ceramic. Even paper rendered water-impervious (e.g. oil paper), can be used. Flexible plastics are particularly useful because they are inexpensive, easy to handle, and provide sufficient support for the reaction membrane and absorbent body. Additionally, flexible plastic can be easily cut or punched to form the open port. Suitable plastics include nylon, Mylar, acrylic sheets, polyester sheets, polyvinyl sheets, etc.

In the simplest embodiment of the invention, a single circular open port is cut into the top support layer, as depicted in FIGS. 1, 2, 4a, and 5a, however the open port can be any other suitable shape. Also, a single top support layer may have more than one open port, so as to form multiple sample receiving wells upon assembly. This allows a single analytical device to be used for testing multiple analytes in a single sample and/or multiple samples. Thus, it will be appreciated that the configuration of the open port(s) can vary depending upon the intended use of the analytical device.

The porous reaction membrane is sealed to the lower surface of the top support layer such that, the rim surrounding the open port and the exposed upper surface of reaction membrane define a sample receiving well. Thus, referring to FIG. 2 which depicts one embodiment of the analytical device after assembly, a portion of the reaction membrane's upper surface (14) is exposed so that when the analytical assay is performed, the sample to be tested and the assay reagents can be added directly to the reaction membrane. The reaction membrane is sized to completely cover the open port. Preferably the reaction membrane will be the same shape as the open port and sized only slightly larger than the open port so that it can be sealed to the lower surface of the top support layer at the periphery of the open port. However, the shape of the reaction membrane and the shape of the open port can differ as shown in FIGS. 4 and 6–8.

FIGS. 4 through 11 show some of the infinite possible configurations for the open port (11) of the top support layer (10) and upper surface (14) of the reaction membrane (13). In the simplest embodiment, referring to FIG. 4a and 4c, the top support layer has a circular open port and the reaction membrane is also circular. However, as shown in FIG. 4c, the reaction membrane does not have to be the same shape as the open port. The larger dot (22) at the center of the reaction membrane depicts the location where receptor is immobilized, and the smaller dot (23) depicts where a control substance is located. The relative shapes and sizes of the receptor and control areas are not important so long as they can be distinguished from each other. Rather than using different sizes of receptor and control dots, positional markers on the surface of the top support layer can accomplish this. In some situations, there may be no need to have a control area on the reaction membrane. Thus, may be convenient to have the receptor immobilized onto the entire exposed surface of the reaction membrane. This is depicted in FIG. 4d, where the inner circle represents the exposed portion of the upper surface of the reaction membrane, and the unshaded area outside the inner circle depicts the unexposed portion of the reaction membrane that is adhered to the lower surface of the top support layer.

Figure 11A:
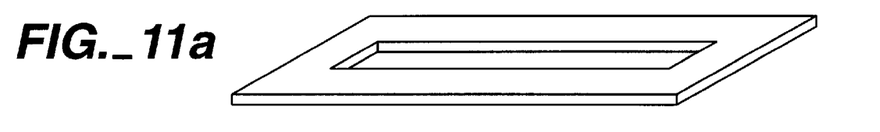
Figure 11B:
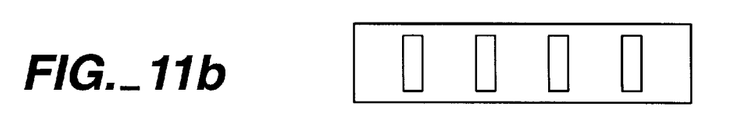

While dots are the simplest configuration for immobilizing the receptor and/or controls, because they can be formed merely by adding drops of receptor and/or control reagents to the membrane surface(s), other shapes can also be used. For example, in U.S. Pat. No. 4,916,056, the receptor area forms a bar, and the negative control forms a bar that crosses the receptor bar such that after the immunoassay is performed a "minus" sign indicates the absence of target substance in the sample tested and a "positive" sign indicates the presence of target substance in the sample. FIG. 11b depicts a sample membrane having multiple receptors immobilized in the shape of parallel bars.

Figure 8A:
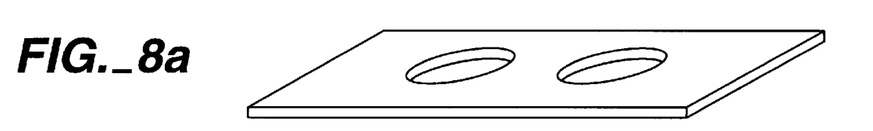
Figure 8B:
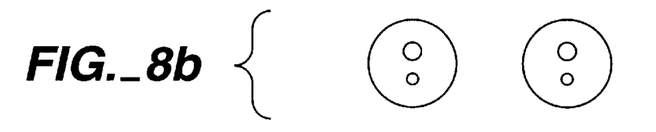
Figure 8C:
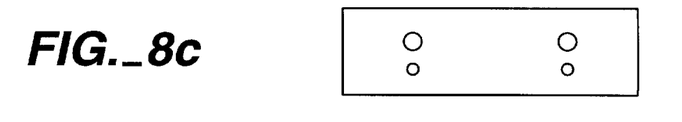
Figure 9A:
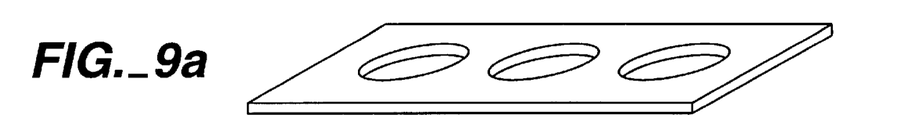
Figure 9B:
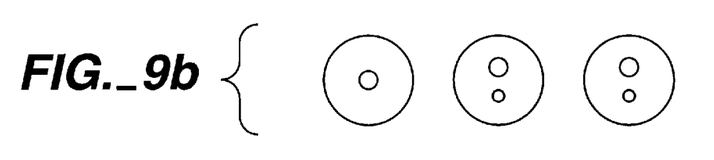
Figure 10A:
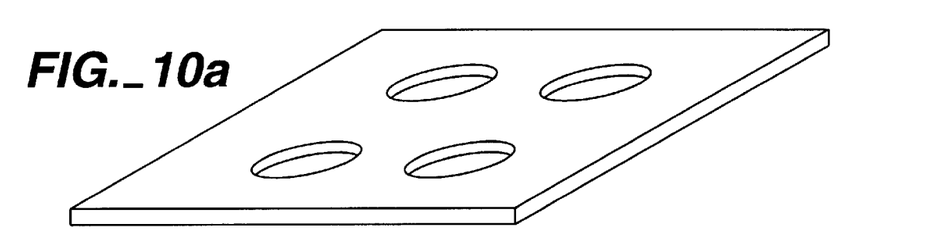
Figure 10B:
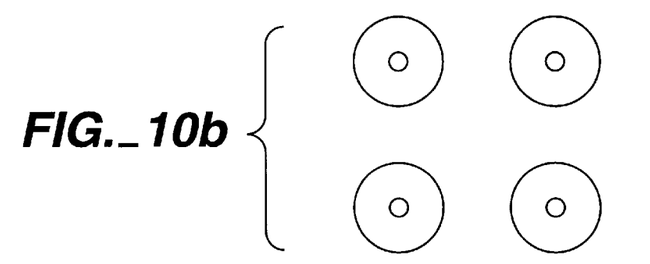

As discussed above, multiple sample receiving wells can be formed as depicted in FIGS. 8, 9 and 10, so that a single sample can be tested for more than one target substance, by inoculating a portion of the sample into each sample receiving well and performing a separate assay for each target substance. Alternatively, a single analytical device with more than one sample receiving well can be used to test for the presence of the same target substance in different samples. A separate membrane can be placed beneath each open port, as depicted in FIGS. 8b, 9b, and 10b. Alternatively, a single reaction membrane, with multiple receptor and control areas can be used as depicted in FIG. 8c.

In some immunoassays, one assay procedure can be performed to test multiple analytes present in a single sample, such that only one sample receiving well is necessary. FIGS. 5, 6, 7 and 11 depict embodiments of the analytical device that can be used in an immunoassay of this type.

Figure 2:
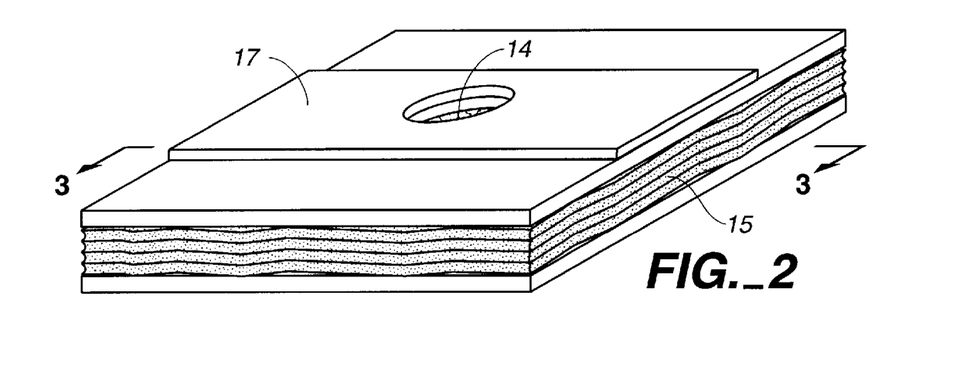
FIG. 2 is a top view of analytical device in accordance with the present invention.
Figure 3:
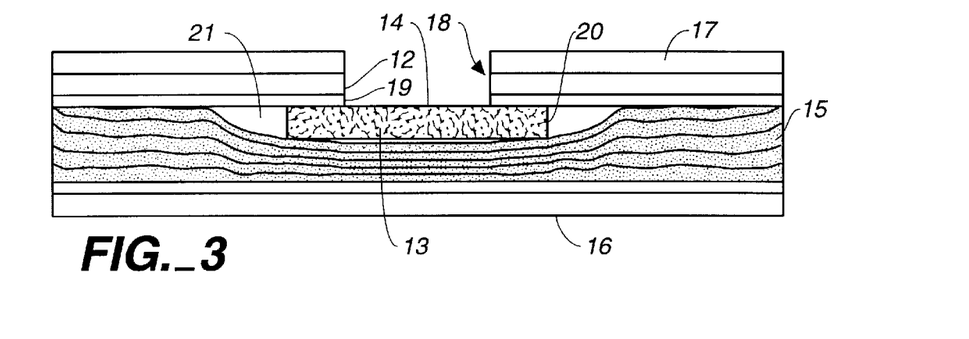
FIG. 3 is a cross section elevation view of the layers of the analytical device of FIG. 2 along the plane 3—3.
Figure 4A:
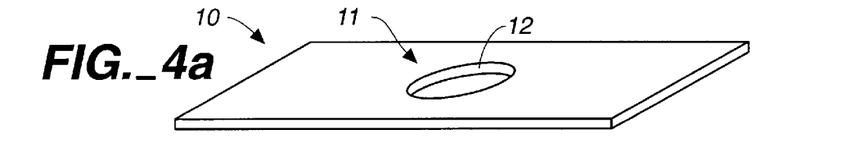
FIGS. 4a–4d, 5a–5c, 6a–6c, 7a–7c, 8a–8c, 9a, 9b, 10a, 10b, 11a, and 11b depict different configurations for the top support layer and reaction membrane.
Figure 4B:
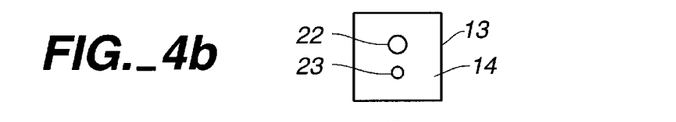
Figure 4C:
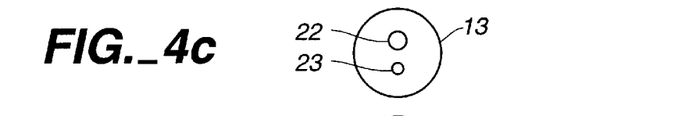
Figure 4D:
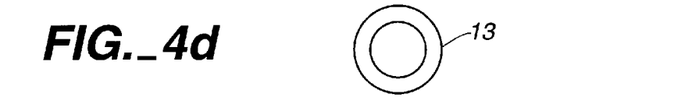
Figure 5A:
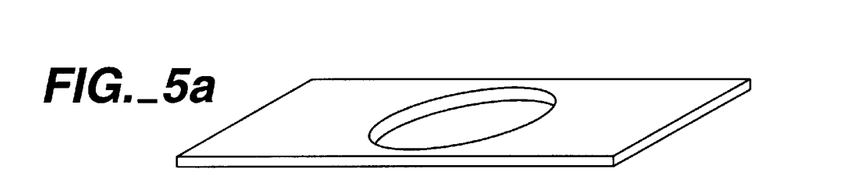
Figure 5B:
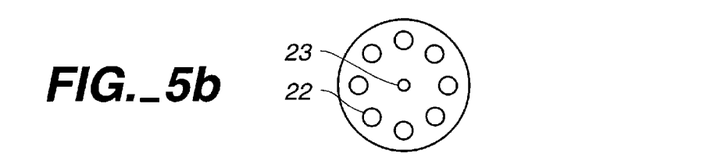
Figure 5C:
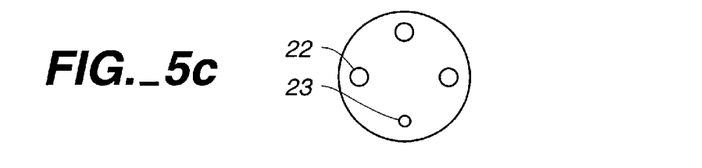
Figure 6A:
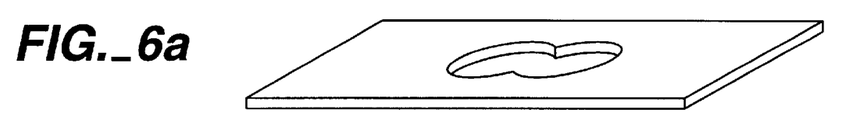
Figure 6B:
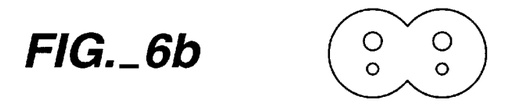
Figure 6C:
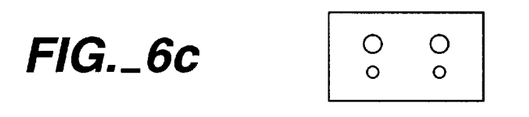
Figure 7A:
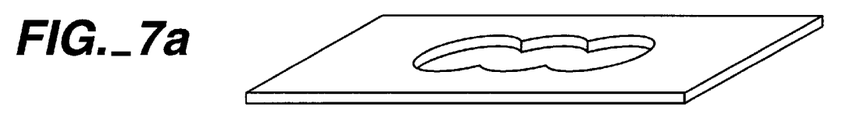
Figure 7B:
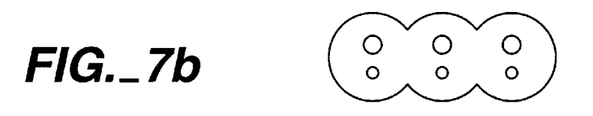
Figure 7C:
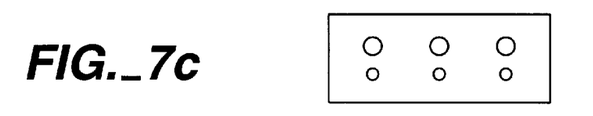

The height of the sample-receiving well rim can be increased, in order to increase the capacity of the sample receiving well or to reduce the possibility of sample spillage. This can be done simply by increasing the thickness of the top support layer, or by attaching a reservoir defining member (17), as depicted in FIGS. 2 and 3, to the upper surface of the top support layer. The reservoir defining member is formed from any water-impervious material which can be the same as or different from the material used to form the top support layer. It has an open port having the same diameter and shape as the open port of the top support layer. Referring to FIG. 3, the open port of the reservoir defining member and the open port of the top support layer are mated so as to define a sample receiving well rim (18).

For the reaction membrane, any suitable porous material capable of immobilizing the receptor reagent employed in the analytical assay, can be used. Suitable materials include nitrocellulose, glass fiber, polyester, cellulose nitrate, polyester, polycarbon, nylon, and other natural and synthetic materials which can be coupled directly or indirectly to the selected receptor. Usually the membrane will comprise positive and/or negative charges that allow the receptor molecule to bind. Certain membrane materials are charged, such as cellulose nitrate which has partial negative charges contributed by the nitro groups. Other materials may be pre-treated to provide a charged membrane. For example, polyester can be derivatized with carboxyl or amino groups to provide either a negatively or positively charged membrane. Nylon can be treated with acid to break peptide bonds to provide positive charges (from the amine groups) and negative charges (from the carboxyl groups).

The term "reaction membrane" is intended to include the porous material to which the receptor reagent employed in the analytical assay is bound as well as additional porous supporting material, if any, that forms the lower surface of the reaction membrane. For example, a preferred reaction membrane comprises a sheet of nitrocellulose backed with a porous paper. Commercially available porous polyester supported nitrocellulose can also be used. A representative example of paper-backed nitrocellulose is commercially available from EY Laboratories Inc. (San Mateo, Calif.; Cat. Nos. PBNC15-1, PBNC15-10, PBNC15M-1, and PBNC15M-10). This preferred membrane is substantially more durable than nitrocellulose alone and can be employed without any other support component. This allows for easier handling and device assembly. Additionally, it has been found that analytical devices employing paper-backed nitrocellulose for the reaction membrane have enhanced sensitivity in certain immunoassays.

Porosity of the membrane has a large influence on the flow rate of the liquid and sensitivity of the assay. The larger the pore size of the membrane, the faster the flow rate for a given liquid. As the flow rate increases, the interaction time available between the target molecule in the sample and the receptor immobilized on the reaction membrane decreases, thus decreasing assay sensitivity. Additionally, larger pore sizes provide less surface area for immobilizing the receptor molecule, which is another parameter attributable to decreased assay sensitivity. For most assays, the porosity of the membrane is preferably in the range of about 0.1 to about 12 microns, and more preferably about 0.45 to 3 microns.

The wicking power of the membrane may affect assay sensitivity and depends on the thickness and nature of the membrane material. Wicking power can be measured as the migration of a standard solution through a certain distance per unit time. Oftentimes, assay sensitivity can be increased by selecting a membrane having a relatively low wicking power.

Referring to FIG. 3, the unexposed upper surface of the reaction membrane is sealed to the lower surface of the top support layer with a water-insoluble adhesive (19) so as to form a liquid-impervious seal between the rim (12) of the top support layer around the open port and the unexposed upper surface (14) of the reaction membrane. The term "liquid-impervious seal" means that when sample and subsequent reagents are added to the sample receiving well, liquid tends to flow through the reaction membrane into the absorbent body below, rather than laterally across the membrane to the unexposed top surface of the reaction membrane. The liquid-impervious seal thus minimizes lateral flow of the sample across the membrane. Thus, the need to utilize compression between the membrane and the absorbent body to force downward flow of the sample through the membrane and into the absorbent body is averted. Downward flow of the sample assists in concentrating the sample through the center of the reaction membrane where the receptor is typically immobilized after the analytical apparatus is assembled. It also slows down the flow rate through the membrane which increases the amount of time that target substance, if present in the sample, is in contact with the receptor. This provides increased sensitivity of the immunoassay employing the analytical device.

Any water-insoluble adhesive, now known or later discovered, can be used in the present invention so long as it is capable of forming a liquid-impervious seal between the rim of the sample receiving well and the unexposed periphery of the upper surface of the reaction membrane. Because of their ease of handling, pressure-sensitive adhesives are preferred. A pressure sensitive adhesive coated onto a surface can form a permanent adhesive film surface which, under slight pressure, adheres immediately to various other surfaces at room temperature. Household masking tape and Scotch™ brand clear tape are examples of products that are made with pressure-sensitive adhesives. Examples of suitable water-insoluble pressure sensitive adhesives include those based on polyacrylic acid or polyvinyl derivatives, natural or synthetic rubbers, and polysiloxanes. The particular type of pressure-sensitive adhesive used is not important except that different adhesives may vary in cost, making less expensive adhesives more preferable. One-sided adhesive tape such as household masking tape or surgical tape can be used in the practice of the present invention. The non-adhesive side of the tape forms the upper surface of the top support layer and the reaction membrane is adhered to the adhesive side. Sheets of clear plastic having pressure sensitive adhesive coated on one side can also be used.

An absorbent body (15) is positioned proximal to the lower surface of the reaction membrane so as to be in liquid communication with the reaction membrane. Thus, the upper surface of the absorbent body may be immediately adjacent to the lower surface of the reaction membrane. Alternatively, there may be an intermediate layer between the reaction membrane and the absorbent body provided that the intermediate layer allows for the transfer of liquid from the reaction membrane to the absorbent body. As one example of an intermediate layer, a porous material may be inserted between the reaction membrane and absorbent body to provide additional support for the reaction membrane. As another example of an intermediate layer, a liquid impervious septum having openings therein so as to further direct sample flow through the center of the reaction membrane can be used. Such septums are described in U.S. Pat. No. 5,006,464. In embodiments of the invention where ease of manufacture and reduced costs are desired, the upper surface of the absorbent body is typically immediately adjacent the lower surface of the reaction membrane.

Any conventionally employed absorbent material that is capable of drawing or wicking liquid through a porous membrane, such as, for example, by capillary action, can be used in the present invention. Useful known materials include cellulose acetate fibers, polyester, polyolefin or other such materials. Layers of commercially available filter paper or bathroom tissue can be also used. The absorbent body provides a means to collect the sample by providing uniform "suction" to deliver the sample from the well, through the reaction membrane, and down into the absorbent body. Thus, the absorbent body also acts as a reservoir to hold the sample, and various reagents that are used when the assay is performed. Accordingly, when used in assays where relatively large volumes of liquid are used, the absorbent body should have high absorbent capacity so as to prevent or minimize the possibility of back-flow of sample and reagents from the absorbent body back into the reaction membrane.

As with the reaction membrane, the wicking power of the absorbent body can be an important parameter. Wicking time is defined in terms of the time required for water to travel a defined distance (7.5 cm) through the absorbent paper and is related to the basis weight, thickness, and composition of the paper. Wicking power can vary greatly from one material to the next. Thus, the properties of the analytical device and flow rate of sample and reagents can be modified by varying the absorbent material used.

The surface area of the upper surface of the absorbent body will usually be greater than that of the reaction membrane, so that the upper surface of the absorbent body can be attached to the lower surface of the top support layer.

Typically the same water-insoluble adhesive used to adhere the reaction membrane to the top support layer is also used to adhere the absorbent body to the top support layer. The water-insoluble adhesive holds the structure together with minimal compression pressure on the absorbent body and reaction membrane, thus avoiding the effects of compression pressure already mentioned.

Referring again to the reaction membrane, in addition to its porosity, its diameter and thickness may effect assay sensitivity. Preferably, the reaction membrane has a surface area that is just slightly larger than the open port of the top support layer, such that the unexposed surface of the reaction membrane has an average diameter of less than 8 mm, preferably less than 3 mm, wherein, referring to FIG. 3, the diameter of the unexposed area is the distance from the exposed surface of the reaction membrane to the side-wall (20) of the reaction membrane.

The thickness of the reaction membrane (i.e. "side-wall" (20), which is the distance between the upper and lower surfaces of the reaction membrane) can vary depend upon the flow characteristics needed for a given immunoassay. Typically, the thickness will range from about 0.05 mm to about to 3.0 mm., and more commonly from about 0.1 to about 1.0 mm. With some immunoassays, it has been found that when the thickness of the reaction membrane is greater than about 0.1 mm, and preferably in the range of about 0.2 mm to about 1.0 mm, higher sensitivity can be achieved. When a sufficiently thick reaction membrane is used, an air-pocket (21) is formed by the lower surface of the top support layer, the side-wall of the reaction membrane, and the upper surface of the absorbent body. It is believed that the enhanced sensitivity is achieved because there is no absorbent material immediately adjacent the side-wall of the reaction membrane which would tend to draw added sample away from the center of the membrane. Thus, the air-pocket further facilitates the downward flow of added sample through the reaction membrane. Additionally, a thicker reaction membrane may allow more receptor to be available for binding to the target substance, thereby providing a further increase in assay sensitivity. It is believed that prior art devices that have relatively thin reaction membranes, such as nitrocellulose membranes less than 0.1 mm thick which are not paper-backed, tend to allow the sample to flow sideways across the reaction membrane rather than downwards through the middle of the reaction membrane. This may be particularly true with devices held together under compression and where the reaction membrane has less surface area than the underlying absorbent body such that a sensitivity-increasing air-pocket is not achieved and the absorbent material comes in contact with the side-wall of the reaction membrane, thus facilitating sideways flow of sample across the reaction membrane and into the absorbent material.

The analytical device of the present invention may further comprise a liquid-impervious bottom support layer (16) which is attached to the lower surface of the absorbent body. The bottom support layer is typically comprised of the same material as the top support layer, although it may be different. As has already been noted, typical prior art analytical devices are comprised of top and bottom housing members which are fitted together so as to hold the reaction membrane and absorbent body in place using compression. Because the reaction membrane and absorbent body of the analytical device of the present invention are adhered to the top support layer using water-insoluble glue, there is no need to utilize compression to hold them together. Thus, there is no need to use fitted or otherwise sealed top and bottom housing members, although sealed or fitted housing members could serve as the top and bottom support layers of the analytical device of the present invention if so desired. In one embodiment of the invention, the top and bottom support layers are not fitted together and are not in contact with each other, such that each side of the analytical device is "open" and the sides of the absorbent body are visible. This is shown in FIG. 2 wherein the absorbent body (15) is visible at the sides of the analytical device.

Because the design of the analytical device is relatively simple compared to that of prior art devices, the material cost is lower and the manufacturing process easier. Multiple analytical devices can be prepared simultaneously. For example, if flexible plastic is used to form the top support layer, a strip of the plastic can be obtained that is long enough to form the desired number of devices. For example, a strip long enough to form 5 support layers can be obtained. Next, 5 evenly spaced holes would be cut into the plastic. The top support layer may be purchased with water-soluble adhesive already adhered to the lower surface, or the adhesive may be applied during the manufacturing process. Most conveniently, the adhesive will be applied to the entire lower surface of the top support layer. Alternatively, the adhesive can be applied just around the open port of the top support layer and around the perimeter of the lower surface of the top support layer so that the reaction membrane and absorbent body can adhere to it.

Continuing with this example, 5 pre-cut reaction membranes would be placed over the open port. A strip of absorbent material would then be adhered to the exposed lower surface of the top support layer, forming the absorbent body. Finally, if a bottom support layer is to be used, material used to form the bottom support layer would be adhered to the lower surface of the absorbent body, preferably with a water-insoluble adhesive. Finally, the assembled strip would be cut so as to form 5 individual analytical devices.

As a variation to the above manufacturing method, the material used to form the bottom support layers could have adhesive applied thereon. Next, the material that forms the absorbent bodies could be attached. A separate strip could be prepared that comprises the material that forms the top support layers and the reaction membranes. The material for the top support layers would have pre-cut holes for the open port, and water-insoluble adhesive applied to the lower surface of the top support layer material. The reaction membranes could then be placed over the open ports and adhered to the lower surface of the top support material by the adhesive. The strip of absorbent material and bottom support material could then be attached to the lower surface of the top support layer/reaction membrane strip. The assembled laminate would then be cut into individual analytical devices. One skilled in the art will of course appreciate that there are many different ways that the devices could be assembled. For example, rather than using strips, where a row of analytical devices are simultaneously assembled, large squares of material could be used so that rows and columns of analytical devices are prepared simultaneously and then subsequently cut into individual devices.

Figure 12:
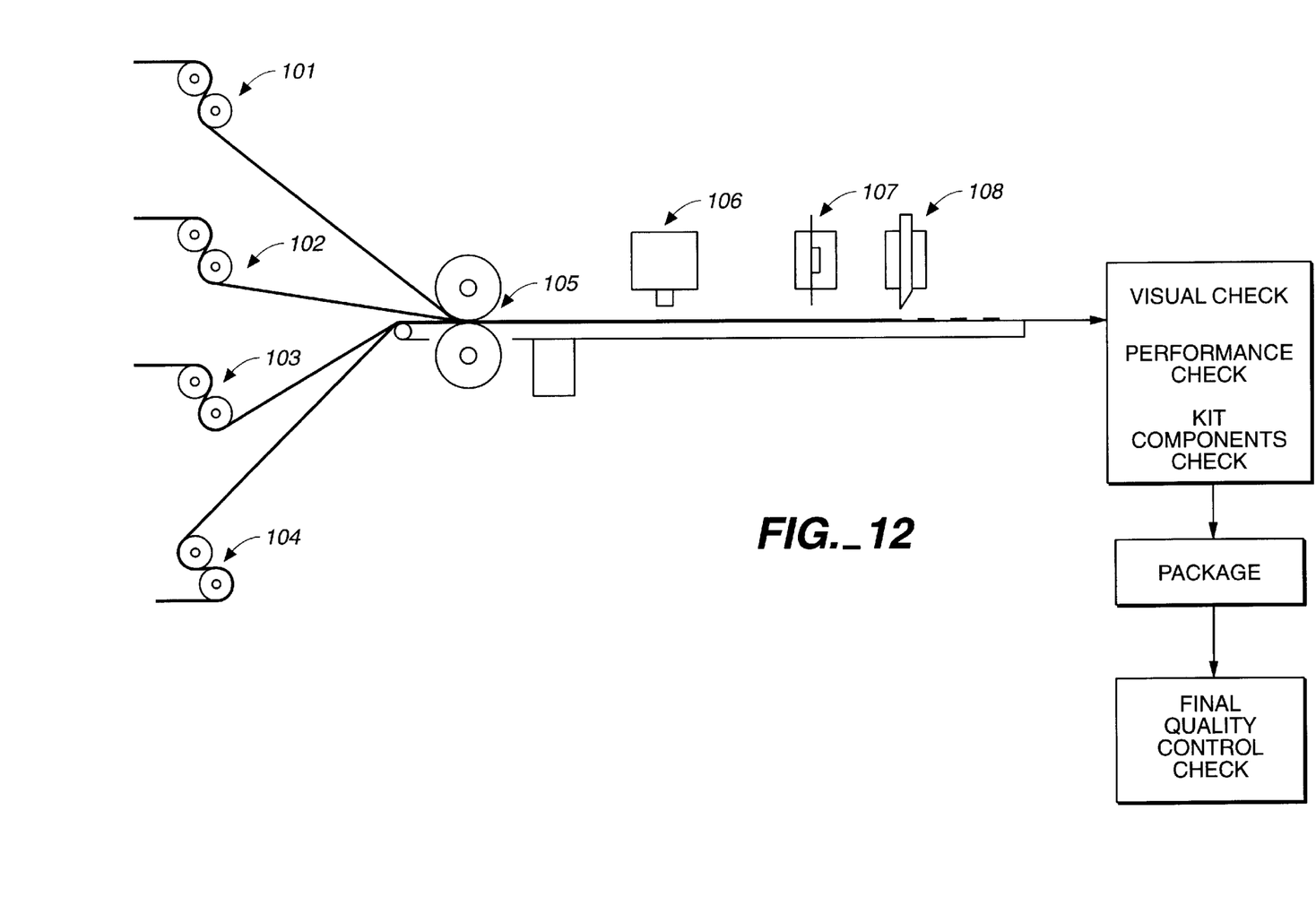
FIG. 12 depicts a manufacturing schematic for the analytical device.

The simple design of the analytical device makes it possible to use rollers for assembly, as shown in FIG. 12. The material that forms the flexible top support layer, having pressure-sensitive adhesive coated on one side and pre-cut holes (for the sample-receiving well) is on one roller (101). The next roller (102) contains the material for the reaction membrane, pre-cut to a suitable width. A third roller (103) is for the material that forms the absorbent body, and a fourth roller (104) is for the material that forms the bottom support layer, which also has pressure-sensitive adhesive coated on one side. The various components are assembled together using a roller press (105). After the four components are joined together, the top support layer may be labeled with a labeling or bar-code device (106) to indicate the type of test for which the device is to be used. An inoculator (107) can inoculate the reaction membrane of the assembled analytical device with the appropriate receptor. Finally, a cutting device (108) can cut individual analytical devices. Other modifications or treatments to the analytical device, which are not depicted in FIG. 12, may occur during assembly or after cutting. For example, the reaction membranes of the analytical devices may then be subject to further treatments such as blocking steps. Finally, various quality control procedures would be followed prior to packaging the devices until ready for use.

The receptor, in the case of immunoassays, is capable of specifically binding to the target substance in a biological sample such as urine, blood, or saliva. One of ordinary skill in the art will appreciate that the term "specific binding" refers to the joining together of substances that fit together such as an antigen and antibody directed thereto. It will also be appreciated that the term "receptor" depending upon the context, may refer to a single molecule capable of specifically binding to a target substance that may be present in a liquid sample. However, the term can also refer to a sufficient number or concentration of receptor molecules necessary to achieve detection of the target substance. When the target molecule is a particular antibody, the receptor will be the antigen for which that antibody is specific. Thus, as used herein, the term "antigen" refers to any substance capable of eliciting an immune response and includes, but is not limited to, Human Immunodeficiency Virus (HIV) antigens, Hepatitis virus antigens (HCV, HBV, HAV), *Toxoplasmosis gondii*, Cytomegalovirus, *Helicobacter pylori*, Rubella, and the like. In some cases, the target molecule will be an antigen, and the receptor will be an antibody that specifically binds to the antigen. The receptor can be applied to the reaction membrane directly, and become immobilized thereon, or coated onto microparticles, such as latex beads, which are then entrapped by the reaction membrane. Suitable methods for applying the receptor to the reaction membrane are known in the art.

In addition to the receptor, a defined area of the exposed reaction membrane may also contain a control molecule. For example, Protein A can be used as a suitable control to determine whether the immunoassay has been performed properly. The use of Protein A as a control is disclosed in U.S. Pat. No. 5,541,059. Other suitable controls are well known in the art.

As noted above, the receptor and, if used, controls are typically applied only to defined regions of the exposed membrane surface. The receptor will often be inoculated onto the center of the reaction membrane such that the perimeter of the exposed surface of the reaction membrane will not have receptor molecule bound thereto. However, in some situations, it may be appropriate to cover the entire exposed surface of the reaction membrane with the receptor. If receptor is inoculated onto a limited region of the exposed membrane surface, the reaction membrane can be treated with a blocking composition that prevents the target substance and other components of the sample from non-specifically binding to the reaction membrane. For assays where non-specific binding is not problematic, a blocking step will be unnecessary. Also, the use of a good quality paper-backed nitrocellulose may make a blocking step unnecessary in some assays. If a blocking step is needed, a common blocking composition comprises bovine serum albumin (BSA) and/or protein solubilization detergents such as those typically disclosed in chemical catalogs (e.g. VWR Scientific Inc., Philadelphia, Pa.). BSA is usually used in amounts from about 1 to 10% and detergents are usually used in amounts from about 0.01 to about 5%. Suitable detergents include polyoxyethylene sorbitan derivatives and polyoxyethylene ethers. A suitable polyoxyethylene sorbitan derivative is polyoxyethylene(20)sorbitan monolaurate (sold as TWEEN 20 by ICI Americas, Inc.). Suitable polyoxyethylene ethers include those sold under the trade name TRITON by Rohm & Haas, such as TRITON X-100.

The membrane blocking treatment typically occurs after the analytical device has already been assembled and the receptor immobilized to the reaction membrane. A sufficient amount of blocking composition to cover the exposed surface of the reaction membrane will be applied to the reaction well. If the reaction well has a diameter of 1 cm, about 50 $\mu$l of the blocking composition should be sufficient. After the blocking composition has dried, the analytical device is ready for use. The analytical device can be packaged until ready for use.

The immunoassays that use the analytical device of the present invention can be very simple and fast, can be qualitative or quantitative. Many different types of immunoassays, known in the art, can be performed using these analytical devices. The analytical devices can be adapted for use in many different types of assays. For example, the target substance can be a hormone, antibody, antigen, protein, etc. A non-inclusive list of possible target substances is provided in U.S. Pat. No. 5,006,464. The immunoassay format, will depend on the target substance sought to be detected. Again, these are already known in the art.

It will be appreciated that in order to maximize sensitivity for the detection of a particular target substance, various components of the analytical device and/or assay procedure can be modified, such as the porosity, thickness and type of material used for of reaction membrane. The blocking and wash solutions and the receptor and detection reagents (e.g. antibody or Protein A labeled with detectable markers such as enzymes, colloidal gold, fluorescent labels, chemiluminescent labels, bioluminescent labels, etc.) will also affect assay sensitivity. The analytical devices can be used in assays that require little to no sample manipulation and that can be performed in less than 1 minute.

All cited references are incorporated herein by reference in their entireties. The following examples and drawings are for illustrative purposes only and are not to be construed as limiting the scope of the invention in any manner.

EXAMPLE 1

Assembly of Analytical Device

This example demonstrates that the analytical devices can be prepared from readily available materials. Plastic sheets with pressure sensitive adhesive coated on one side (Cleer-Adheer® made by C-LINE Products, Inc.) are obtained from a stationary store and cut into 1"×1" squares to form the top support layers of the analytical device. A ⅛" hole is cut into the middle of each square using a hole-puncher. Reaction membrane material, also obtainable from a stationary store (e.g. cellulose paper such as ordinary household paper towels, porous nylon sheets, porous cellulose acetate paper, ink-blotting paper or any other material with good filtration quality), is cut into ¼" circles using a ¼" hole-puncher. The reaction membrane circle is adhered to the adhesive side of the top support layer to cover the ⅛" hole. Absorbent material is obtained having a suitable thickness and cut in 1"×1" squares and adhered to the adhesive side of the top support layer to form the absorbent body. A bottom support layer is prepared from the same pressure sensitive adhesive-coated plastic that is used for the top support layer and adhered to the lower surface of the absorbent body.

EXAMPLE 2

Immunoassay Using Analytical Device to Test IgG

Analytical devices were prepared using the following components and were assembled as shown in FIGS. 1–3: Top support layers measuring 3.8 cm square were cut from flexible, but rigid polyvinyl chloride (PVC) plastic (Tap Plastics retail store) that had a water-insoluble pressure-sensitive adhesive on one side. Holes 8 mm in diameter were punched into the center of the top support layers. Circular reaction membranes, 11 mm in diameter, were punched from paper-backed nitrocellulose having a thickness of approximately 0.8 mm (EY Laboratories Inc. Cat. # PBNC15-1) and adhered to the top support layer so as to cover the hole. An absorbent body comprised of a 3.8 cm square of absorbent material (from Whatman, Cat. No. F427-05) was adhered to the adhesive side of the top support layer. A bottom support layer, measuring 3.8 cm square and comprising the same plastic material and adhesive as the top support layer, was adhered to the lower surface of the absorbent body. A reservoir defining member, comprising the same plastic material and adhesive as the top support layer, measuring approximately 3.8 cm×1.5 cm, and having an 8 mm diameter hole punched in the center, was position onto the top of the top support layer as shown in FIG. 2.

A 1 mg/ml solution of rabbit IgG (EY Catalog # AF541-1) was prepared in phosphate buffered saline (0.05M pH 7.4) containing 1% bovine serum albumin (PBS/BSA diluent). A ½μl drop was spotted onto the center of the exposed surface of the reaction membrane. There was no further treatment of the reaction membrane (e.g. blocking treatment). The IgG solution was allowed to dry. A 6 μg/ml solution of Protein A/colloidal gold (available from EY-Laboratories Inc, Cat. # GP-01, GP-01-100, or FC-PRO-5) was prepared in 0.5% Tween 20 and 50 μl were added to the reaction membrane. A purple-red dot appeared where the IgG had been spotted. The remainder of the reaction membrane remained white. This demonstrates that the analytical device can be used to detect low concentrations of IgG.

The solution of IgG can be serially diluted and each dilution spotted onto the membrane of an analytical device. A standard curve can be generated and the end-point of detection of the assay described above can be determined by performing the assay steps and determining the lowest concentration of IgG that can be visualized. Samples containing unknown quantities of IgG can be tested as above, and the intensity of the resulting red-purple dot (if any) can be compared to the standard curve to obtain semi-quantitative results.

EXAMPLE 3

Immunoassay Using Analytical Device to Test IgG

Analytical devices were assembled as described in Example 2. The reaction membranes of each device were inoculated with 0.5 μl of 1 mg/ml Protein A solution. Serial dilutions of a known concentration of normal human serum were made in the PBS/BSA diluent described in Example 2. An 80 μl drop of each dilution of human serum was added to the reaction membrane and allowed to completely absorb. An 80 μl drop of the Protein A/colloidal gold solution described in Example 2 was added to the reaction membrane and allowed to completely absorb. Distilled water (120 μl) was added to the reaction membrane to wash unbound reagents through the membrane. At the end of the assay, a purple-red spot was visible on the analytical device which was used to test the presence of IgG in a ¹⁄₁₀₀₀ dilution of normal human serum, indicating that IgG was present and detectable at that dilution using the analytical device and the above assay procedures.

What is claimed is:

1. An analytical device for use in assays for the detection of a bindable target substance in a liquid sample potentially containing said target substance, comprising:

(a) a liquid-impervious top support layer having an upper surface and a lower surface, said top support layer defining a rim around an open port;

(b) a porous reaction membrane having an upper surface and a lower surface proximal to said top support layer, a portion of said reaction membrane upper surface and said rim defining a sample receiving well, said reaction membrane upper surface being sealed to the lower surface of said top support layer by water-insoluble adhesive so as to form a liquid-impervious seal therebetween; and (c) an absorbent body having an upper surface and a lower surface, wherein said absorbent body upper surface is proximal to and in liquid communication with the lower surface of said reaction membrane.

2. The analytical device of claim 1 further comprising:

(d) a liquid-impervious bottom support layer having an upper surface that is proximal to the lower surface of said absorbent body.

3. The analytical device of claim 1 wherein said upper surface of said absorbent body extends beyond the periphery of said reaction membrane.

4. The analytical device of claim 2 wherein said liquid-impervious seal is maintained in the absence of compression between said top support layer and said bottom support layer.

5. The analytical device of claim 2 wherein said top support layer and said bottom support layer are not fitted or sealed together.

6. The analytical device of claim 3 wherein said reaction membrane has a side-wall and wherein an air-pocket is formed by the lower surface of said top support layer, said reaction membrane side-wall, and the upper surface of said absorbent body.

7. The analytical device of claim 6 wherein said side-wall of said porous reaction membrane has a height of from about 0.2 to 1.0 mm.

8. The analytical device of claim 1 wherein said water-insoluble adhesive is pressure-sensitive.

9. The analytical device of claim 1 wherein said top support layer comprises a flexible plastic.

10. The analytical device of claim 1 further comprising a reservoir-defining member attached to said upper surface of said top support layer.

11. The analytical device of claim 1 wherein said reaction membrane comprises nitrocellulose.

12. The analytical device of claim 11 wherein the lower surface of said reaction membrane comprises at least one liquid-permeable support material bonded in intimate contact with said nitrocellulose.

13. The analytical device of claim 9 wherein said support material is selected from the group consisting of paper, fiberglass and polyester.

14. The analytical device of claim 1 wherein an exposed area of said upper surface of said reaction membrane has immobilized thereon a receptor capable of directly or indirectly binding to said bindable target substance, said immobilized receptor being concentrated in a limited region of said exposed area of said upper surface.

15. The analytical device of claim 14 wherein said receptor is an antigen or an antibody.

* * * * *